United States Patent [19]

Hosono

[11] 3,948,251

[45] Apr. 6, 1976

[54] FLEXIBLE TUBE ENDOSCOPE

[75] Inventor: Saburo Hosono, Tokyo, Japan

[73] Assignee: Olympus Optical Co., Ltd., Tokyo, Japan

[22] Filed: May 1, 1975

[21] Appl. No.: 573,735

Related U.S. Application Data

[63] Continuation-in-part of Ser. No. 408,846, Oct. 23, 1973, abandoned.

[30] Foreign Application Priority Data

Oct. 25, 1972  Japan.............................. 47-106836

[52] U.S. Cl. ............................ 128/4; 128/6; 128/8
[51] Int. Cl.² ...................... A61B 1/06; F11L 11/18
[58] Field of Search .................................... 128/4–9

[56] References Cited

UNITED STATES PATENTS

| | | | |
|---|---|---|---|
| 3,572,325 | 3/1971 | Bazell et al. ............................ | 128/6 |
| 3,670,721 | 6/1972 | Fukami et al. ........................... | 128/6 |
| 3,799,152 | 3/1974 | Kim ....................................... | 128/6 |

*Primary Examiner*—Aldrich F. Medbery

[57] ABSTRACT

A flexible tube device has a flexible tube one end of which is connected to a distal end and the other end of which is connected to a control unit, a central tube formed by coiling a metal strip and provided within and coaxially with the flexible tube, and an adjusting mechanism provided within the control unit to control the pliability of the flexible tube from the outside by varying the diameter of the central tube.

7 Claims, 3 Drawing Figures

3,948,251

FLEXIBLE TUBE ENDOSCOPE

CROSS-REFERENCE TO RELATED APPLICATION

This application is a continuation-in-part application of U.S. pat. application Ser. No. 408,846 filed Oct. 23, 1973 and now abndoned.

BACKGROUND OF THE INVENTION

This invention relates to a flexible tube device for an endoscope, and particularly to a flexible tube device applicable to a wider usage.

Generally known is a flexible endoscope as inserted into a stomach, small intestine etc. to effect observation, examination and medical treatment of which a flexible tube is designed to insert a distal end into the interior of the human body and which has merely a predetermined pliability or flexibility. For this reason it is impossible to freely vary the pliability of the flexible tube according to the conditions under which it is used. This inflicts wide limitation on the usage of the endoscope. Suppose, for example, that the flexible tube is inserted through an anus into a colon for observation. Then it is preferred that the flexible tube portion be somewhat pliable as far as it is passed through an S-shaped colon. However, difficulty is presented in inserting it further into the interior of the human body, since its additional inserting force causes the flexible tube to be sagged or slacked to prevent any further insertion. If in such a case the pliability of the flexible tube can be freely adjusted to permit further insertion, then an endoscope finds a still wider application.

SUMMARY OF THE INVENTION

It is accordingly the object of this invention to provide a simple flexible tube device for an endoscope, capable of freely and controllably varying the pliability of a flexible tube to a desired extent by a simple operation. The flexible tube device according to this invention is used in an endoscope having a distal end, introduced by the flexible tube device into the interior of the human body and a control unit for effecting various operations necessary for the endoscope, and comprises an outer flexible tube member, a central tube member formed by coiling a strip member and disposed within the outer flexible tube member and extending along the longitudinal direction thereof, and an operating section connected to one end of the central tube member and operated at the control unit to vary the pliability of the flexible tube by varying the diameter of the central tube member.

The flexible tube device according to this invention is not required for its whole length to be of necessity made equal to the whole length of the outer tube member. That is, it is only necessary that the outer tube member constitute at least part of the whole length of the flexible tube device. Generally, a flexible tube device for an endoscope includes either a bendable section and a flexible tube or a flexible tube only. The same can be said of the flexible tube device according to this invention.

Detailed Description of the Invention

Figure 1:
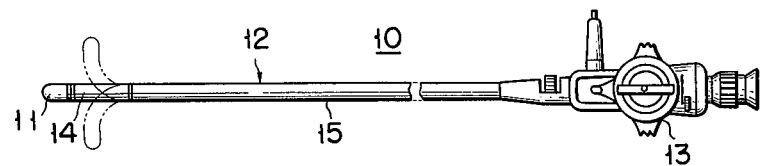
FIG. 1 is a side view of an endoscope with a flexible tube device according to this invention as applied to an endoscope.

In FIG. 1 an endoscope 10 is constructed by a distal end 11, a flexible or pliable tube 12 connected to the distal end at one end so as to introduce the latter into the interior of the human body, a control unit 13 connected to the other end of the flexible tube and adapted to effect, from the outside, various operations necessary for the endoscope 10. The flexible tube 12 has a bandable section 14 situated at the forward end and a connecting section for connecting together the bendable section 14 and the control unit 13. The control unit 13 has an eyelens and light source connecting section, respectively, optically connected to an observation window and illumination window (not shown) provided in the distal end 11, as well as a knob for operating the bendable section and an inlet for introducing a forceps.

Figure 2:
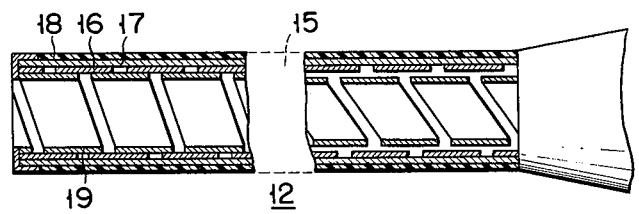
FIG. 2 is a partial, cross sectional view of the flexible tube device of FIG. 1.

As shown in FIG. 2, the connecting section 15 of the flexible tube 12 comprises an outer flexible tube 18 housing an inner tube 16 formed by closely coiling an elongated metal strip, and a sheath 17 covering the outer periphery of the inner tube 16. The sheath 17 is formed by knitting together fine metal wires or synthetic resin wires into a fabric. The outer tube 18 is made of a pliable synthetic resin which is pliably bendable. Although a combination of the inner tube 16, sheath 17 and outer tube 18 presents a very good flexible tube, this invention should not be restricted to this flexible tube. The flexible tube according to this invention may also be formed from a combination of the inner tube and outer tube, a combination of the sheath and outer tube, or the outer tube only.

Within the flexible tube is substantially coaxially disposed a central tube or coil tube 19 formed by closely coiling an elongated metal strip or band. The central tube 19 is somewhat spaced apart from the inner surface of the inner tube 16 when the connecting section is in the most pliable state. However, when the central tube 19 needs its outer diameter to be increased for reasons to be described later, the central tube 19 is abutted against the inner surface of the inner tube 16 under a corresponding force so that the pliability of the connecting section 15 is restricted. The first coil tube 16 is opposite in its spiral direction to that of the second coil tube 19. The bendable section 14 of the tube 12 may be made of such material as used in the flexible tube or may be made of an entirely different material so that it can be later connected to the remaining portion of the flexible tube. The forward end of the central tube 19 is firmly fixed to the inner surface of the forward end of the flexible tube and the base portion of the central tube 19 extends into the control unit 13.

Figure 3:
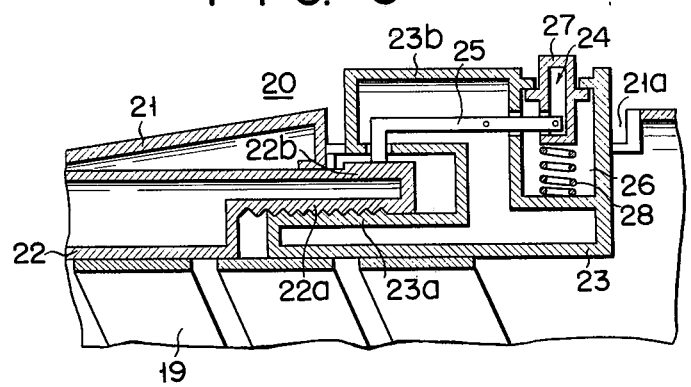
FIG. 3 is a partial, cross sectional view showing part of an adjusting mechanism for adjusting the pliability of the flexible tube device.

Within the control unit 13 is provided a mechanism 20, as shown in detail in FIG. 3, for controlling or adjusting the diameter of the coil tube 19 or the compressibility. The mechanism 20 is provided within a cylindrical part 21 extending from the main body of the control unit 13.

Within the forward end portion of the extending cylindrical body 21 is coaxially secured a fixed cylindrical body 22 whose forward end is connected to the coil tube 16, sheath 17 and outer tube 18 of the flexible tube. The second coil tube 19 coaxially extends through the cylindrical body 22. Near the terminal end of the cylindrical body 22 is provided a rotational cylinder 23 having substantially the same inner diameter as that of the cylinder body 22. The projecting portions projecting from the confronting surfaces of the cylinder bodies 22 and 23 have screw threaded portions 22a and 23a which are meshed with each other. Within the rotational cylinder body 23 is secured the base end of the coil tube 19 extending through the fixed cylinder body 22. As a result, the rotation of the rotational cylinder body 23 causes it to be moved in the axial direction to permit the diameter or compressibility of the central tube or second coil tube 19 to be varied. Thus, the pliability of the flexible tube can be varied. In the peripheral wall of the cylindrical portion 21 is provided a partial annular opening 21a. The handle portion 23b of the rotational cylinder body 23 projects from the annular opening 21a and is movable to a certain extent in the circumferential direction. The handle portion 23b is equipped with a holding mechanism 24 for holding the rotational cylinder body 23 at a predetermined angle. The holding mechanism has a swing lever 25 whose substantially middle portion is pivoted by a pin. One end of the lever 25 extends through the side wall of the handle portion into a pocket 26 provided in the top surface of the handle portion and the extension end of the lever 25 is pivoted below a push botton 27. The push botton 27 is normally upwardly urged by a coil spring 28 disposed between the push button 27 and the bottom surface of the pocket 26. The pocket and button have respective engaging projections to prevent the button from being bounced out from the pocket under the urging force of the coil spring. The other end of the swing lever 25 projects from the bottom surface of the handle portion 23b and is engaged, when in a holding position, with projecting portions 22b extending in a longitudinal direction and disposed in parallel with each other. When it is desired to change the diameter of the coil tube 19 through the adjustment mechanism, the button 27 is depressed against the force of the spring 28 to permit the swing lever to be disengaged from the engaging portions 22b of the fixed cylinder 22. Then, the rotational cylinder 23 is rotated to a certain extent through the operation of the handle portion 23b to cause it to be moved in the axial direction. As a result, the diameter of the coil tube 19 is changed to an extent corresponding to the movement of the rotational cylinder to permit the pliability of the flexible tube to be varied.

There will be explained more in detail the control of the pliability of the flexible tube through the use of the coil tube 19.

When the diameter of the second coil tube 19 is minimal, the outer surface of the coil tube 19 is spaced somewhat apart from the first coil tube 16. As a result, the pliability of the connecting section 15 depends entirely upon the members constituting the flexible tube and is not influenced by the second coil tube 19. Thus, the connecting section exhibits the most pliable state. The gradual increase in diameter of the second coil tube 19 causes it to be gradually abutted against the inside wall of the first coil tube 16 to permit the pliability of the flexible tube to be restricted.

Suppose that, for example, a colon is examined using an endoscope having such a construction. The distal end of the endoscope is inserted through an anus into an S-shaped colon in a manner that the flexible tube has a relatively high pliability, and then further inserted into the interior of the human body after passage of the S-shaped colon in a manner that the flexible tube has a relatively low pliability. In this way, the distal end attached to the flexible tube can be easily carried into the sinuous or serpentine S-shaped colon and further into the interior of the human body.

A mechanism for controlling the flexing of the flexible tube 12 through adjustment of the diameter of the coil tube 19 is not limited to that arranged as described above, but may consist of the form constructed by providing the undermentioned modification for the device shown in, for example, FIG. 3.

Namely, engagement between the fixed cylinder body 22 and rotational cylinder body 23 is effected by an assembly of annular grooves and the corresponding annular ridges in place of the threaded portions 22a, 23a, thereby preventing the cylindrical body 23 from making an axial movement, but only allowing it to rotate. The central tube 19 is connected to the cylindrical body 23 by thread engagement. The abovementioned arrangement causes the central tube 19 to be axially drawn or contracted relative to the cylindrical body 23 when it is rotated, thereby attaining the same effect as the aforesaid mechanism.

What is claimed is:

1. A flexible tube device for an endoscope having a distal end and a control unit, comprising a flexible tube, one end of which is connected to the distal end and the other end of which is connected to the control unit; and a central coaxial tube in the form of a continuous helical strip member disposed within the flexible tube and also connected to said distal end and engageable with said flexible tube, both along the longitudinal direction thereof; and a means to stiffen and relax rigidity of the device comprising an adjusting mechanism to which one end of the central tube is operatively connected for providing longitudinal movement between the tubes to control the pliability and the flexing of the flexible tube by varying the diameter of the central tube to cause an abutting force against the flexible tube to be varied as required.

2. A device according to claim 1, in which said flexible tube includes an outer flexible tube and an inner tube in the form of a continuous helical strip member disposed within the outer flexible tube.

3. A device according to claim 2, in which said inner tube is provided on its outer periphery with a sheath of resilient fabric restraining its radial movement.

4. A device according to claim 2, in which said inner tube in the form of a helical strip member is coiled in a direction opposite to that of the central tube of like form.

5. A device according to claim 1, in which said control unit has a fixed cylindrical body secured to the flexible tube and through which one end of the central tube extends, and a movable cylindrical body adjacent to and coaxially with the fixed cylindrical body connected to the end of the central tube and movable to vary the diameter of the central tube.

6. A device according to claim 5, in which said movable cylindrical body is rotatably mounted on the control unit, and connected to the fixed cylindrical body to be axially moved when it is rotated.

7. A device according to claim 6, in which said mechanism has a holding mechanism for holding the movable cylindrical body in a predetermined rotational position relative to the fixed cylindrical body.

* * * * *